(12) United States Patent
Koh et al.

(10) Patent No.: US 9,566,358 B1
(45) Date of Patent: Feb. 14, 2017

(54) STERILIZATION APPARATUS

(71) Applicant: Industrial Technology Research Institute, Hsinchu (TW)

(72) Inventors: Zhi-Wei Koh, Taichung (TW);
Chien-Chun Lu, New Taipei (TW);
Chun-Hsing Lee, Hsinchu (TW);
Chen-Peng Hsu, Hsinchu (TW)

(73) Assignee: Industrial Technology Research Institute, Hsinchu (TW)

(*) Notice: Subject to any disclaimer, the term of this patent is extended or adjusted under 35 U.S.C. 154(b) by 0 days.

(21) Appl. No.: 14/958,863

(22) Filed: Dec. 3, 2015

(30) Foreign Application Priority Data

Sep. 25, 2015 (TW) .............................. 104131954 A

(51) Int. Cl.
*A61L 2/10* (2006.01)

(52) U.S. Cl.
CPC ...................................... *A61L 2/10* (2013.01)

(58) Field of Classification Search
USPC ............................ 250/453.11, 454.11, 455.11
See application file for complete search history.

(56) References Cited

U.S. PATENT DOCUMENTS

| | | | |
|---|---|---|---|
| 6,475,433 B2 | 11/2002 | McGeorge et al. | |
| 7,090,779 B2 | 8/2006 | Bernstein et al. | |
| 7,361,904 B2 | 4/2008 | Cassassuce et al. | |
| 7,416,588 B2 | 8/2008 | Burrows et al. | |
| 7,695,675 B2 | 4/2010 | Kaiser et al. | |
| 8,421,032 B2 | 4/2013 | Dornseifer | |
| 2006/0241364 A1 | 10/2006 | Ince | |
| 2010/0224562 A1 | 9/2010 | Rolchigo et al. | |
| 2010/0237254 A1 | 9/2010 | Mason et al. | |
| 2014/0050612 A1 | 2/2014 | Kneissl et al. | |

FOREIGN PATENT DOCUMENTS

| | | |
|---|---|---|
| CN | 102318872 | 1/2012 |
| CN | 103720192 | 4/2014 |
| CN | 103787447 | 5/2014 |

(Continued)

OTHER PUBLICATIONS

"Office Action of Taiwan Counterpart Application", issued on Jun. 28, 2016, p. 1-p. 5.

(Continued)

*Primary Examiner* — Nicole Ippolito
*Assistant Examiner* — Hanway Chang
(74) *Attorney, Agent, or Firm* — Jianq Chyun IP Office

(57) ABSTRACT

In an embodiment, a sterilization apparatus, adapted to sterilize a liquid to be sterilized, comprises a first sterilization light source, a first container and a sterilization container. The first sterilization light source includes a carrier, a plurality of LED packages and a plurality of collimating units, wherein the plurality of LED packages are disposed on and electrically connected to the plurality of carriers, and each of the plurality of collimating units separately is disposed on a corresponding LED package. The first container accommodates the first sterilization light source, and defines a first light-mixing space. The sterilization container includes an accommodating space for accommodating the liquid, wherein the first container is assembled together with the sterilization container, and the first light-mixing space is disposed between the first sterilization light source and the accommodating space.

20 Claims, 4 Drawing Sheets

(56) References Cited

FOREIGN PATENT DOCUMENTS

| CN | 203575874 | 5/2014 |
|---|---|---|
| TW | M357978 | 6/2009 |
| TW | M368376 | 11/2009 |
| TW | M488747 | 10/2014 |
| TW | M492608 | 1/2015 |

OTHER PUBLICATIONS

Michael Kneissl, et al., "Development of UV-LED Disinfection," TECHNEAU, Feb. 2010, pp. 1-36.
I. Gaska, et al., "Efficiency of Point-of-Use Water Disinfection Using Deep UV Light Emitting Diode Technology," TechConnect World Conference & Expo, Jun. 13-16, 2011, pp. 1-4.
John C. H. Chang, et al., "UV Inactivation of Pathogenic and Indicator Microorganisms," Applied and Environmental Microbiology, vol. 49, No. 6, Jun. 1985, pp. 1361-1365.
Stephen A. Craik, et al., "Inactivation of Giardia Muris Cysts Using Medium-Pressure Ultraviolet Radiation in Filtered Drinking Water," Water Research, vol. 34, No. 18, Dec. 15, 2000, pp. 4325-4332.
Michael S. Shur, et al., "Deep-Ultraviolet Light-Emitting Diodes," IEEE Transactions on Electron Devices, vol. 57, No. 1, Jan. 2010, pp. 12-25.
Colleen Bowker, et al., "Microbial UV fluence-response assessment using a novel UV-LED collimated beam system," Water Research, vol. 45, No. 5, Feb. 2011, pp. 2011-2019.

STERILIZATION APPARATUS

CROSS-REFERENCE TO RELATED APPLICATION

This application claims the priority benefits of Taiwan application serial no. 104131954, filed on Sep. 25, 2015. The entirety of the above-mentioned patent application is hereby incorporated by reference herein.

TECHNICAL FIELD

The technical field relates to a sterilization apparatus, adapted to sterilize a liquid to be sterilized.

BACKGROUND

The ultraviolet (UV) light was discovered in 1801. In 1877, British scientists used the UV light to irradiate and kill *Bacillus subtilis* and *Bacillus*, which confirmed the ultraviolet disinfection. Deep UV lights with the wavelength ranged from 200 nm to 280 nm could directly damage the links of the deoxyribonucleic acid (DNA) and the Ribonucleic acid (RNA) in the bacteria and the viruses, and the sterilization effect is unrelated to the bacterial species. The sterilization efficiency may be ranged from 99% to 99.9%. Among these deep UV lights, the UV light of the wavelength ranged from 250 nm to 270 nm has the strongest sterilization effect.

The sterilization effect of the UV light is related to the irradiance, the irradiation time and the conditions of the object to be sterilized. Although enhancing the irradiance and the irradiation time of the UV light could increase the sterilization effect, the non-uniform distribution of the irradiance and the long irradiation time would not like to be seen by the designer or the user. Therefore, how to enhance the sterilization efficiency and the sterilization effectiveness of the UV light under an appropriate irradiance and an irradiation time becomes one of the important issues to be solved.

SUMMARY

An embodiment of the disclosure relates to a sterilization apparatus, adapted to sterilize a liquid to be sterilized. The sterilization apparatus comprises a first sterilization light source, a first container and a sterilization container. The first sterilization light source includes a carrier, a plurality of light-emitting diode (LED) packages and a plurality of collimating units, wherein the plurality of LED packages are disposed on and electrically connected to the carrier, and each of the plurality of collimating units separately is disposed on a corresponding LED packages. The first container accommodates the first sterilization light source, and defines a first light-mixing space. The sterilization container includes an accommodating space for accommodating the liquid to be sterilized, wherein the first container is assembled together with the sterilization container, and the first light-mixing space is disposed between the first sterilization light source and the accommodating space.

The foregoing will become better understood from a careful reading of a detailed description provided herein below with appropriate reference to the accompanying drawings.

DETAILED DESCRIPTION OF DISCLOSED EMBODIMENTS

Figure 1:
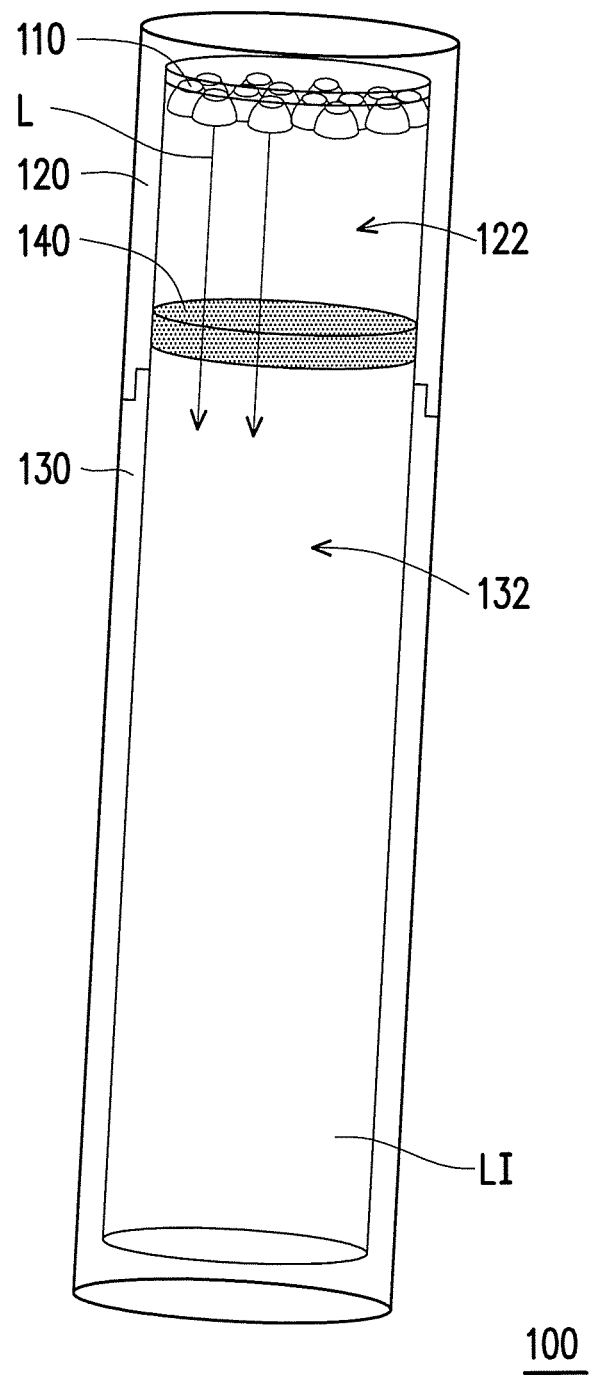
FIG. 1 is a schematic diagram of a sterilization apparatus, according to an embodiment of the disclosure.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

Figure 2:
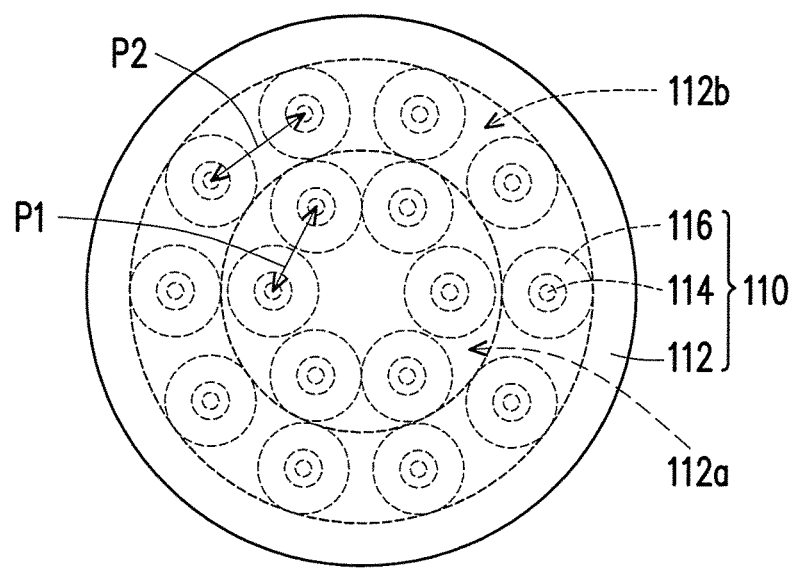
FIG. 2 is a top view of a schematic diagram of a first sterilization light source of the FIG. 1.

FIG. 1 is a schematic diagram of a sterilization apparatus, according to an embodiment of the disclosure. FIG. 2 is a top view of a schematic diagram of a first sterilization light source 110 of the FIG. 1. Please refer to FIG. 1 and FIG. 2, a sterilization apparatus 100 is adapted to sterilize a liquid LI to be sterilized. The liquid LI to be sterilized for example is water, aqueous solution or other liquid. The sterilization apparatus 100 of the disclosure includes a first sterilization light source 110, a first container 120 and a sterilization container 130. The first sterilization light source 110 includes a carrier 112, a plurality of light-emitting diode (LED) packages 114 and a plurality collimating units 116. The plurality of LED packages 114 are disposed on and electrically connected to the carrier 112. Each of the collimating units 116 is correspondingly disposed on one of the plurality of LED packages 114. The first container 120 accommodates the first sterilization light source 110, and defines a first light-mixing space 122. The sterilization container 130 includes an accommodating space 132 for accommodating the liquid LI to be sterilized. The first container 120 is assembled together with the sterilization container 130 such that the first light-mixing space 122 is between the first sterilization light source 110 and the accommodating space 132. In the embodiment, each light L emitted from the first sterilization light source 110 is first mixed completely in the first light-mixing space 122, and then emits toward the liquid LI to be sterilized in the accommodating space 132.

The first sterilization light source 110 may provide a first minimum irradiance for a top of the accommodating space 132 in the sterilization container 130, wherein the top is the place closest to the first sterilization light source 110 and the first minimum irradiance is Amin. Also, the first sterilization light source 110 may provide a second minimum irradiance for a bottom of the accommodating space 132 in the sterilization container 130, wherein the bottom is the place farthest from the first sterilization light source 110 and the second minimum irradiance is Cmin. The Amin and the Cmin may satisfy at least one of the following formulas (1), (2) and (3):

$$[2\times|Amin-Cmin|/(Amin+Cmin)]\times 100\% < 25\% \quad (1)$$

$$[2\times|Amin-Cmin|/(Amin+Cmin)]\times 100\% < 20\% \quad (2)$$

$$[2\times|A\text{min}-C\text{min}|/(A\text{min}+C\text{min})]\times 100\% < 15\% \qquad (3)$$

In the embodiment, a depth of the accommodating space 132 may be, but not limited to larger twice than a width of the accommodating space 132. For example, when the accommodating space 132 is a cylindrical space, the width of the accommodating space 132 may be a diameter of a circular cross-section. When the accommodating space 132 is a space of polygonal columnar or other shapes, the width of the accommodating space 132 may be defined as, but not limited to a largest straight-line distance between any two points on the polygonal. In the embodiment, the bottom of the accommodating space 132 may be, but not limited to a flat plane or a curved plane. The curved plane may be a spherical, a parabolic surface, and so on.

In the embodiment, the carrier 112 in the first sterilization light source 10 may be, but not limited to a circuit board. The circuit board may include the circuit for driving the plurality of the LED packages 114, and the circuit for example may be, but not limited to a power integrated circuit (IC), an electro static discharge (ESD) protector, wirings electrically connected to driving the plurality of the LED packages 114, passive components. The carrier 112 may selectively set a portable power, such as mercury batteries, lithium batteries, fuel cells, etc., for driving the plurality of the LED packages 114 to emit light. In another embodiment, the carrier 112 may use an external power to drive the plurality of the LED packages 114 to emit the light, and the embodiment is not limited thereto.

In an embodiment of the disclosure, the sterilization apparatus 100 may be a cup having sterilization characteristics, and the cup may include a lid and a cup-type body. In other words, the shape of the first container 120 of the sterilization apparatus 100 may be, for example, made into a shape of the lid, the sterilization container 130 of the sterilization apparatus 100 may be, for example, made into a cup-type body, and the lid and the cup may be assembled together in any kind of ways. The lid may include the first sterilization light source 110 to sterilize the liquid inside the cup. The sterilization apparatus 100 in the embodiment may be adapted to sterilize the liquid LI in the cup. The sterilization apparatus 100 may also be adapted to a water filter system to sterilize the liquid LI that is passing through the sterilization apparatus 100 and to be sterilized. In an embodiment of applying the sterilization apparatus 100 to the water filter system, a plurality of fluid in-outlets may be set on the first container 120 and the sterilization container 130 of the sterilization apparatus 100, respectively. Therefore, when the liquid LI to be sterilized passes through the sterilization apparatus, the liquid LI may be sterilized.

The first container 120 and the sterilization container 130 may moderately reflect the light from the first sterilization light source 110 to enhance the sterilization effect.

In an embodiment of the disclosure, the sterilization apparatus 100 may further include a first optical substrate 140 assembled together with the first container 120. The first optical substrate 140 separates the first light-mixing space 122 and the accommodating space 132, and the first light-mixing space 122 is between the first sterilization light source 110 and the first optical substrate 140. For example, the first optical subtract 140 may be, but not limited to a quartz subtract or other kinds of optical substrates made by a transparent material having a specific durability to the UV light. In the embodiment, the first optical substrate 140 may not only allow the light emitted from the first sterilization light source 110 passing through, but also prevent the first sterilization light source 110 from contacting the liquid LI to be sterilized. This further protects the first sterilization light source 110.

As shown in the FIG. 2, the carrier 112 has a central area 112a and a surrounding area 112b. The central area 112a is adjacent to the surrounding area 112b and is surrounded by the surrounding area 112b. For example, the shape of the carrier 12 is a circle, the central area is a circular area and the surrounding area 112b is a ring area. In addition, the center of the central area 112a and the center of the carrier 112 are overlapping, and the area of the central area 112a is ranged from 25% to 40% of the total area of the carrier 112.

In an embodiment of the disclosure, the number of the LED packages 114 distributed in the central area 112a is less than that of the LED packages 114 distributed in the surrounding area 112b. As shown in an example of FIG. 2, the number of the LED packages 114 distributed in the central area 112a is six, and the number of the LED packages 114 distributed in the surrounding area 112b is ten, but the embodiment is not intended to limit the disclosure. For example, the number of the LED packages 114 distributed in the central area 112a may be ranged from three to six, and the number of the LED packages 114 distributed in the surrounding area 112b may be ranged from four to ten. Also, an arrangement pitch P1 of the LED packages 114 distributed in the central area 112a is for example less than an arrangement pitch P2 of the LED packages 114 distributed in the surrounding area 112b. In addition, the number of the LED packages distributed in the central area 112a or in the surrounding area 112b may be one or more.

Accordingly, the designs for the number and the distribution mode of the LED packages distributed in central area 112a and in the surrounding area 112b and the light-mixing space 122 are required to follow the principle of increasing the distribution uniformity of light L, to achieve uniformly illuminating the liquid LI to be sterilized.

Figure 3:
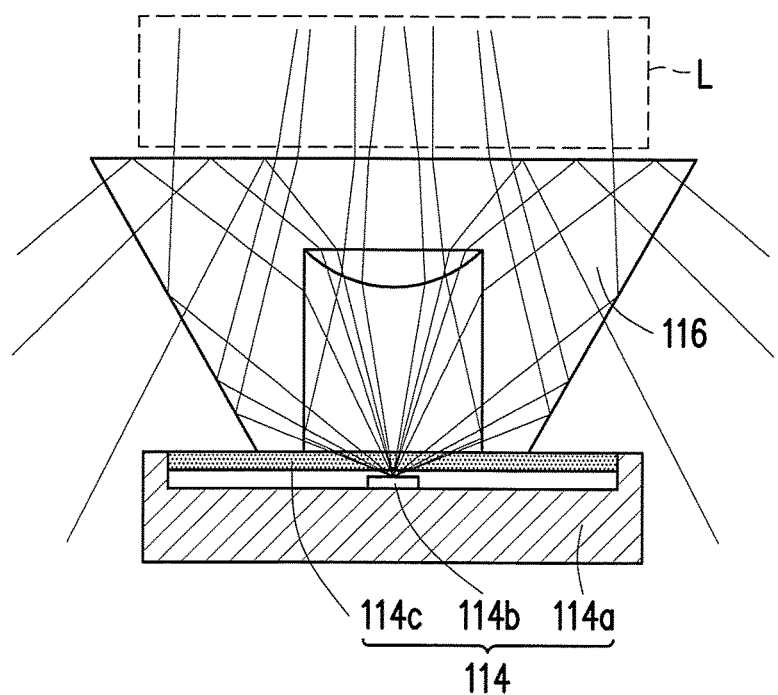
FIG. 3 is a cross-sectional view of a light emitting diode package and a collimating unit of the FIG. 1.

FIG. 3 is a cross-sectional view of a light emitting diode package and a collimating unit of the FIG. 1. Please refer to an embodiment of FIG. 3, each of LED packages 114 includes a package substrate 114a, at least one LED chip 114b and a package unit 114c. The at least one LED chip 114b is disposed on and electrically connected to the package substrate 114a, and the package unit 114c is disposed on the package substrate 114a to cover the LED chip 114b. The package substrate 114a may be, but not limited to a ceramic circuit board, the LED chip 114b may be, but not limited to a UV LED chip, and the material of the package unit 114c is may be, but not limited to glass or other transparent material with a specific durability to the UV light. In an embodiment, a cover glass board is covered on the LED chip 114b, and an optical adhesive is filled in the space between the cover glass board and the LED chip 114b, thus the LED chip 114b is covered with the optical adhesive. In other words, the package unit 114c includes the cover glass board and the optical adhesive. In another embodiment, there is no the optical adhesive filled between the cover glass board and the LED chip 114b, namely, the package unit 114c serves as the cover glass board. Each of the plurality of the LED packages 114 is suitable for emitting a ultraviolet (UV) light and the wavelength of the UV light is ranged from 260 nm to 285 nm, which is the wave band of a deep UV light or a UV-C light.

As illustrated in FIG. 3, the collimating unit 116 in the embodiment may be, but not limited to a lens or other optical unit that may collimate the light L emitted from the LED package 114. In the embodiment, the aforementioned lens may be, but not limited to a total internal reflection lens (TIR lens), and other optical unit which could that may collimate the light L may be, but not limited to a reflecting cup with a parabolic reflecting plane. The collimating unit 116 may enhance the directivity of the light L emitted from each of the plurality of the LED packages 114. When the light L emitted from the LED package 114 passes through the collimating unit 116, the degree of divergence of the light is decreased. This may prevent energy loss and has a better sterilization effect. Also, the collimating unit 116 in the embodiment may enhance the irradiance of the light L emitted from the LED package 114 more than 25%. In the embodiment, the material of the collimating unit 116 may be, but not limited to quartz material. This may enhance the tolerance and the reliability of the UV light of the collimating unit 116.

Figure 4A:
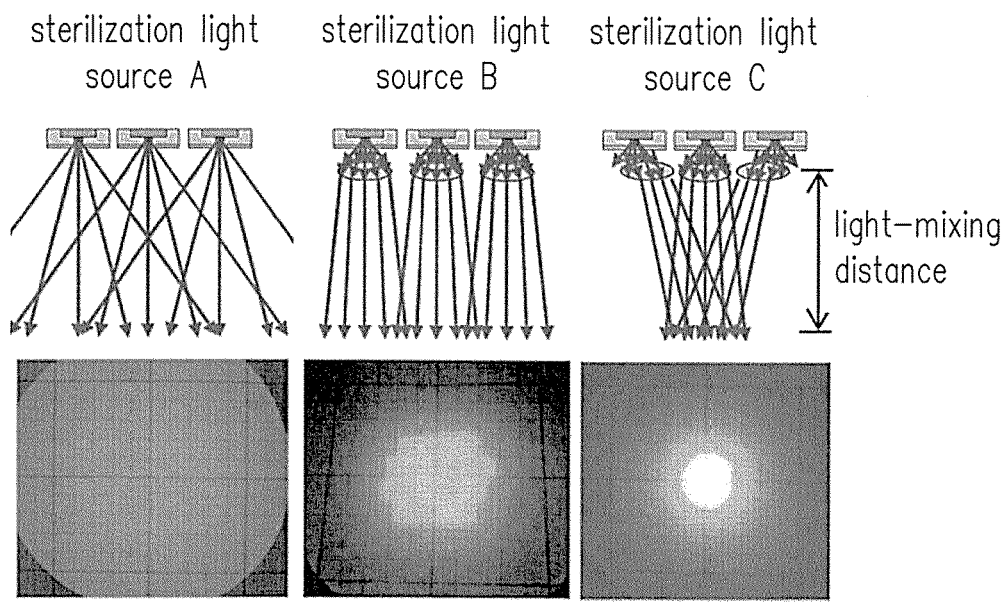
FIG. 4A is a schematic diagram of different designs of the sterilization light source according to embodiments of the disclosure.
Figure 4B:
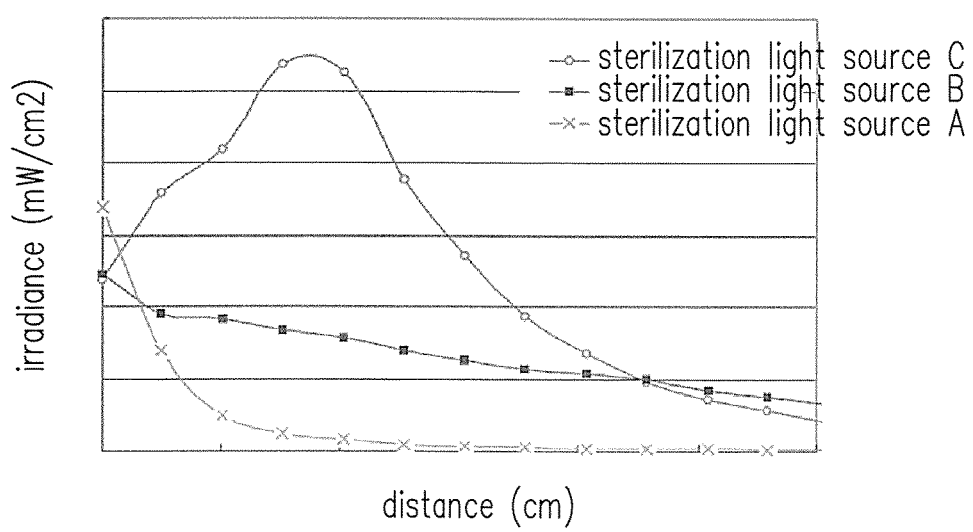
FIG. 4B is a relation diagram between the irradiance and the distance with under different designs of the sterilization light source of the disclosure.

FIG. 4A is a schematic diagram of different designs of the sterilization light source of the disclosure, and FIG. 4B is a relation diagram between the irradiance and the distance under different designs of the sterilization light source of the disclosure. Please refer to FIG. 4A, on the left side of FIG. 4A, a sterilization light source A does not include a collimating unit, and the light emitted from the sterilization light source A has a quite large degree of divergence. In the middle part of FIG. 4A, a sterilization light source B includes a collimating unit, and the light adjusted by passing through the collimating unit and is relatively convergent compared with the left side of FIG. 4A. On the right side of FIG. 4A, a sterilization light source C includes a collimating unit, and the light adjusted by passing through the collimating unit is more convergent compared with the left side and the middle part of FIG. 4A. In other embodiments, the light emitted from the sterilization light source may be parallel by passing through the collimating unit.

Please referring to FIG. 4A and FIG. 4B, the irradiance of the light L provided by the sterilization light source A may dramatically decrease as the transfer distance increases. Therefore, the light L of the sterilization light source A without the collimating unit has a very limited transfer distance, and the sterilization effect is also limited. In contrast, each of the sterilization light sources B and C having the collimating unit performs significantly better than the sterilization light source A in the aspect of the irradiance. In other words, the light L provided by each of the sterilization light sources B and C having the collimating unit has better collimation and sterilization effects.

Figure 5:
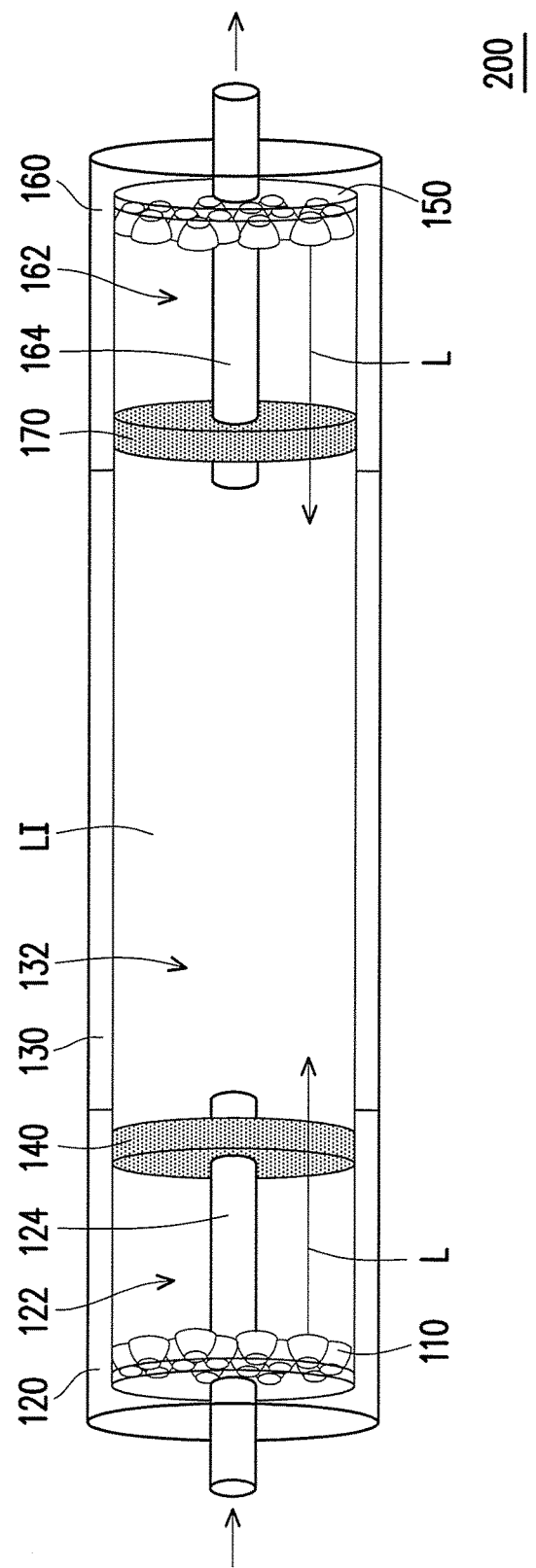
FIG. 5 is a schematic diagram of a sterilization apparatus, according to another embodiment of the disclosure.

FIG. 5 is a schematic diagram of a sterilization apparatus, according to of another embodiment of the disclosure. Please refer to FIG. 5, the sterilization apparatus 100 in FIG. 1 is similar to the sterilization apparatus 200 in the embodiment of FIG. 5. The main difference between the two is that the sterilization apparatus 200 in FIG. 5 further includes a second sterilization light source 150 and a second container 160. The second sterilization light source 150 is accommodated in the second container 160. The second container 160 defines a second light-mixing space 162, and the second container 160 is assembled together with the sterilization container 130 so that the sterilization container 130 is between the first container 120 and the second container 160. The light L emitted from the second sterilization light source 150 may completely mix in the second light-mixing space 162 and then emit toward the liquid LI to be sterilized in the accommodating space 132. In the embodiment, the sterilization apparatus 200 has the first sterilization light source 110 and the second sterilization light source 150; therefore, the sterilization effect of the sterilization apparatus 200 is optimized.

The sterilization apparatus 200 in the embodiment may further includes a second optical substrate 170 assembled together with the second container 160. The second light-mixing space 162 and the accommodating space 132 is separated by the second optical substrate 170, and the second light-mixing space 162 is between the second sterilization light source 150 and the second optical substrate 170. For example, the second optical substrate 170 is a quartz substrate or other kind of optical substrate made by a transparent material having a specific durability to the UV light. The second optical substrate 170 in the embodiment may allow the light emitted from the second sterilization light source 150 passing through, but also preventing the second sterilization light source 150 from contacting the liquid LI to be sterilized. This protects the second sterilization light source 150.

The sterilization apparatus 200 in the embodiment may be adapted to a cup to sterilize the liquid LI to be sterilized. Also, the sterilization apparatus 200 may be adapted to a water filter system to sterilize the liquid LI that is passing through the sterilization apparatus 200 and to be sterilized.

In an embodiment of applying the sterilization apparatus 200 to a water filter system, the first container 120 in the embodiment includes a first fluid in-outlet 124 connecting the accommodating space 132, the second container 160 includes a second fluid in-outlet 164 connected to the accommodating space 132. After setting the first in-outlet 124 and the second in-outlet 164, the liquid LI to be sterilized may be sterilized when it passes through the sterilization apparatus 200. For example, the first in-outlet 124 is through the first sterilization light source 110 and the second in-outlet 164 is through the second sterilization light source 150.

In summary, the sterilization apparatus in the disclosure performs the sterilization by using the sterilization light source such as the LED, designing the appropriate light-mixing space and cooperating with the use of the collimating unit, such that the light emitted from the sterilization light source may more effectively irradiate the liquid to be sterilized. This achieves a good sterilization effect. The sterilization apparatus in the disclosure may be adapted to the water filter system, kettles, cups, and so on.

It will be apparent to those skilled in the art that various modifications and variations can be made to the disclosure. It is intended that the specification and examples be considered as exemplary embodiments only, with a scope of the disclosure being indicated by the following claims and their equivalents.

What is claimed is:

1. A sterilization apparatus, adapted to sterilize a liquid to be sterilized, the sterilization apparatus comprising:
   a first sterilization light source, including a carrier, a plurality of light-emitting diode (LED) packages and a plurality of collimating units, wherein the plurality of LED packages are disposed on and electrically connected to the carrier, and each of the plurality of collimating units separately is disposed on a corresponding LED packages;
   a first container accommodating the first sterilization light source, wherein the first container defines a first light-mixing space; and
   a sterilization container, including an accommodating space for accommodating the liquid to be sterilized, wherein the first container is assembled together with the sterilization container, and the first light-mixing space is disposed between the first sterilization light source and the accommodating space.

2. The sterilization apparatus of claim 1, wherein the carrier includes a central area and a surrounding area, and the central area is adjacent to and surrounded by the surrounding area.

3. The sterilization apparatus of claim 2, wherein a number of the plurality of LED packages in the central area is less than that of the plurality of LED packages in the surrounding area.

4. The sterilization apparatus of claim 3 wherein a shape of the carrier is a circle, the central area is a circular area and the surrounding area is a ring area.

5. The sterilization apparatus of claim 1, wherein each of the plurality of LED packages is adapted to emit an ultraviolet light.

6. The sterilization apparatus of claim 5, wherein the wavelength of the ultraviolet light is ranged from 260 nm to 285 nm.

7. The sterilization apparatus of claim 1, wherein a plurality of lights emitted from the plurality of LED packages of the first sterilization light source converge after passing through the plurality of collimating units.

8. The sterilization apparatus of claim 1, wherein a plurality of lights emitted from the plurality of LED packages of the first sterilization light source are parallel to each other after passing through the plurality of collimating units.

9. The sterilization apparatus of claim 1, wherein the first container further includes a lid and the sterilization container includes a cup.

10. The sterilization apparatus of claim 1, further including:
a first optical substrate assembled together with the first container, wherein the first optical substrate separates the first light-mixing space and the accommodating space, and the first light-mixing space is between the first sterilization light source and the first optical substrate.

11. The sterilization apparatus of claim 1, further including:
a second sterilization light source; and
a second container accommodating the second sterilization light source, wherein the second container defines a second light-mixing space, the second container are assembled together with the sterilization container, and the sterilization container is between the first container and the second container.

12. The sterilization apparatus of claim 11, wherein the first container has a first fluid in-outlet connected to the accommodating space.

13. The sterilization apparatus of claim 12, wherein the first fluid in-outlet is through the first sterilization light source.

14. The sterilization apparatus of claim 12, wherein the second container has a second fluid in-outlet connected to the accommodating space.

15. The sterilization apparatus of claim 14, wherein the second fluid in-outlet is through the second sterilization light source.

16. The sterilization apparatus of claim 15, further including:
a second optical substrate assembled together with the second container, wherein the second optical substrate separates the second light-mixing space and the accommodating space, and the second light-mixing space is between the second sterilization light source and the second optical substrate.

17. The sterilization apparatus of claim 1, wherein the first sterilization light source provides a first minimum irradiance Amin for a top of the accommodating space in the sterilization container, and a second minimum irradiance Cmin for a bottom of the accommodating space in the sterilization container, and the Amin and the Cmin satisfy a formula of $[2\times|Amin-Cmin|/(Amin+Cmin)]\times 100\% < 25\%$.

18. The sterilization apparatus of claim 1, wherein the first sterilization light source provides a first minimum irradiance Amin for a top of the accommodating space in the sterilization container, and a second minimum irradiance Cmin for a bottom of the accommodating space in the sterilization container, and the Amin and the Cmin satisfy a formula of $[2\times|Amin-Cmin/(Amin+Cmin)]\times 100\% < 20\%$.

19. The sterilization apparatus of claim 1, wherein the first sterilization light source provides a first minimum irradiance Amin for a top of the accommodating space in the sterilization container, and a second minimum irradiance Cmin for a bottom of the accommodating space in the sterilization container, and the Amin and the Cmin satisfy a formula of $[2\times|Amin-Cmin|/(Amin+Cmin)]\times 100\% < 15\%$.

20. The sterilization apparatus of claim 1, wherein the collimating unit includes a total internal reflection lens.

* * * * *